(12) United States Patent
Nihipali

(10) Patent No.: US 8,640,311 B2
(45) Date of Patent: Feb. 4, 2014

(54) STEAMATORY, METHOD OF USE, AND MANUFACTURE

(76) Inventor: Kunani Nihipali, Haleiwa, HI (US)

( * ) Notice: Subject to any disclaimer, the term of this patent is extended or adjusted under 35 U.S.C. 154(b) by 678 days.

(21) Appl. No.: 12/878,914

(22) Filed: Sep. 9, 2010

(65) Prior Publication Data

US 2010/0325850 A1    Dec. 30, 2010

Related U.S. Application Data

(60) Division of application No. 11/669,456, filed on Jan. 31, 2007, now Pat. No. 7,805,819, which is a continuation of application No. 10/729,136, filed on Dec. 5, 2003, now abandoned.

(51) Int. Cl.
*A01N 1/00* (2006.01)

(52) U.S. Cl.
USPC .................................................. 27/21.1; 27/1

(58) Field of Classification Search
USPC .............................................. 27/1, 21.1, 23.1
See application file for complete search history.

(56) References Cited

U.S. PATENT DOCUMENTS

| 4,067,091 A * | 1/1978 | Backman ........................ 27/21.1 |
| 2009/0093044 A1* | 4/2009 | Wiigh-Masak ............... 435/262 |

* cited by examiner

*Primary Examiner* — Lynne Anderson

(57) ABSTRACT

A method is used to prepare a body for burial. The method includes placing the body inside a vessel. The body includes bones and tissue. The method further includes subjecting the body to a flow of steam until the bones are free of tissue. In one implementation, the flow of steam has a temperature of about 212 degrees Fahrenheit and a mass flow rate of at least 1000 pounds per hour. The method may further include removing the bones from the vessel.

18 Claims, 2 Drawing Sheets

STEAMATORY, METHOD OF USE, AND MANUFACTURE

CROSS-REFERENCE TO RELATED APPLICATIONS

This application is a divisional application of U.S. patent application Ser. No. 11/669,456, filed Jan. 31, 2007, now U.S. Pat. No. 7,805,819 titled "Steamatory For Preparing A Body For Burial," which is a continuation application of U.S. patent application Ser. No. 10/729,136, filed Dec. 5, 2003, now abandoned titled "Apparatus And Method Of Preparing A Body For Burial," each of which is incorporated by reference herein.

FIELD

The present invention relates in general to preparation of a body for burial and more particularly, to an apparatus and method of preparing a deceased body for burial by separating the flesh from the bone structure through the application of steam.

BACKGROUND

Many cultures have specific beliefs, formalities, and rituals associated with preparing a deceased body for burial or other final arrangements. Some cultures believe in embalming the body, placing the embalmed body into a sealed casket, and then burying the casket. Other cultures believe in cremation where the body is reduced to ashes and then placed in an urn or scattered in a natural setting.

Some cultures place special emphasis on certain parts of the body. The Hawaiian culture believes that, with respect to human remains, the iwi (bones) contain mana (spiritual energy) and must be prepared with the proper respect and dignity. Native Hawaiians have strong family values, responsibilities, and obligations. The family of the deceased has the kuleana (duty and responsibility) to take care of the person who has died and passed on to the next level. Depending on the position and occupation of the deceased in society, the bones are handled in different manners. In some cases, the body is buried wholly with the bones and flesh intact. In other cases, especially for those in a higher level of society, the flesh is removed from the bones and the bones are placed or buried in a huna (secret location). In earlier times, the body was arranged in a fetal or flexed position. At other times, the body was arranged in a fully extended position. If the deceased had been a fisherman, some families would utilize the femur bone to make fishhooks and perpetuate the mana of the fisherman to continue to provide food for the next generation. In any case, through respect and dignity for the dead, the bones must not be disturbed once placed to rest or come outside the control of the family. To disturb the bones would constitute desecration of the ancestral remains and disturbance to the living family.

For those cases where the flesh is to be removed from the bone prior to burial, the deceased is placed in an imu (underground oven). The oven is often a pit dug in the ground and lined with wood and stones. Before the body is placed in the oven, the wood is burned to heat the stones. A bed or layer of leaves is placed over the hot stones and the body is laid upon the bed of leaves. The body is covered with another layer of leaves to keep it clean. The body is cooked by the heated stones which softens the flesh over a period of time. After a day or so, the flesh is sufficiently soft that it can be removed or striped from the body by hand leaving the skeletal remains. By using this steaming process, the moisture and mana stays in the bones. It is then the prerogative of the family as to how to care for the iwi (bones) once the flesh was removed.

SUMMARY

In one embodiment, the present invention is a steamatory for preparing a body for burial comprising a chamber having an access panel. A tray is provided that is at least partially removable from the chamber through the access panel. A plurality of steam ports is disposed within the chamber. A steam generator provides steam to the plurality of steam ports within the chamber. The steam is injected into the chamber causes tissue of the body to separate from bone structure.

In another embodiment, the present invention is an apparatus for preparing a body for burial comprising a vessel adapted for accepting the body. A support structure is disposed within the vessel for supporting the body. A plurality of steam ports is disposed within the vessel. Steam is injected into the vessel causes tissue of the body to separate from bone structure.

In yet another embodiment, the present invention is a method of preparing a body for burial comprising the steps of providing a vessel adapted for accepting the body, placing the body on a support structure disposed within the vessel, and injecting steam through a plurality of steam ports disposed within the vessel to cause tissue of the body to separate from bone structure.

DETAILED DESCRIPTION

When a person dies, many cultures place special emphasis on certain parts of the body. Native Hawaiians believe that, with respect to ancestral remains, the iwi (bones) contain mana (spiritual energy; essence) and must be given proper respect and dignity in the preparation of the body and the burial process. The mana must not be lost, i.e. it must be preserved in the bones.

Native Hawaiians have strong family values, obligations, and responsibilities. The family of the deceased has the duty and responsibility to take care of the person who has died and passed on to the next level. Depending on the position and occupation of the deceased in society, especially for those in a higher level of society, the flesh is removed from the bones. The bones are believed to contain mana (spiritual energy; essence). The energy must be preserved in the bones. The bones must be placed or buried in a safe location to ensure that they are not disturbed once placed to rest or otherwise come outside the control of the 'ohana (family).

In the burial preparation process, including removal of the flesh and tissue from the bones, the body should be handled as little as possible. Moreover, the bones must be kept moist and prevented from drying out which is believed to cause a loss of mana (spiritual energy; essence).

Figure 1:
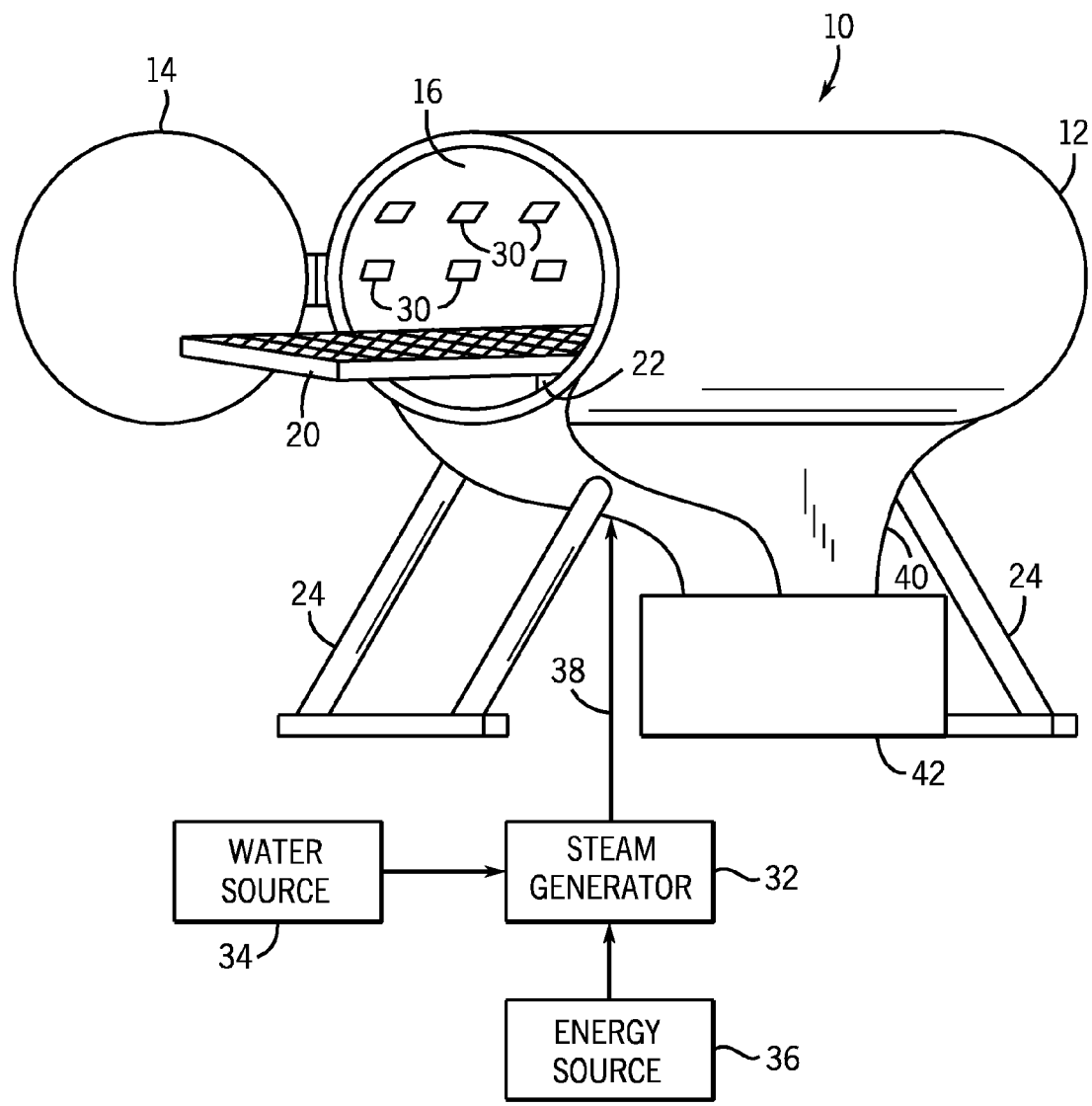
FIG. 1 illustrates a steamatory for preparing a body for burial by separating the tissue from the bones.

Referring to FIG. 1, a body processing chamber or vessel 10, also referred to as a steamatory, is shown as an embodiment of the present invention. The following elements are not necessarily drawn to scale. Chamber 12 is cylindrical in form and includes door or access panel 14 on one end. Door 14 is made of stainless steel and hinged to chamber 12. Chamber 12 is 4 feet in diameter and 10 feet long. The dimensions of the steamatory accommodate a body weight up to 400 lbs. Chamber 10 is made from stainless steel or other metal which is non-corrosive in the presence of steam and heat. Door 14 opens to an inner portion 16 of chamber 12. A tray or sliding rack 20 slides on rollers 22 into and out of inner portion 16. Tray 20 is a support structure for the body. Tray 20 is made from stainless steel in the form of a wire mesh. The mesh of tray 20 provides 0.5 inch openings. Tray 20 may include multiple layers of wire mesh, e.g. two or three separate racks, with graduating sizes of mesh openings from 0.5 inch to 0.125 inch. The racks slide in and out of inner potion 16, independently of one another, with about 2.0 inches of clearance between each rack. The steamatory is stabilized and supported by braces 24.

The body of the deceased is prepared for burial under the authority, control, supervision, care and responsibility of the 'ohana (family). The body of the deceased is disrobed and wrapped with kapa cloth made from wauke (bark of the paper mulberry tree), tissue, paper, or other degradable material, which breaks down and disintegrates in the presence of heat and steam. Door 14 is opened and tray 20 is at least partially removed or pulled from inner portion 16 of chamber 12. The body is carefully laid on tray 20. Alternatively, the disrobed body is laid on the kapa cloth or degradable material and further covered by the same material. The family and/or religious leader conducts any appropriate final ritual over the body. Tray 20 is slid into inner portion 16 and door 14 is closed and sealed.

A plurality of steam jets or ports 30 line the interior walls of chamber 12 for injecting superheated steam into inner portion 16. A steam generator 32 receives water from water source 34 and energy from energy source 36. Energy source 36 can be electrical, propane, natural gas, or other fossil fuel. The energy is utilized by steam generator 32 to heat the water in a boiler under pressure to generate steam. The steam is routed from steam generator 32 through conduit 38 to the steamatory.

With the body of the deceased sealed inside, the steam enters inner portion 16 of chamber 12 through steam jets 30. The steam enters chamber 12 at 212° F. with a mass flow rate of 1000 lbs/hour. In the presence of the superheated steam, the kapa or other degradable material covering the body breaks down and disintegrates over a period of time. The degrading body-covering material falls through the wire mesh of tray 20 into funnel or contoured structure 40. The degrading material continues through funnel 40 into collection container 42.

In addition to the degrading body-covering material, in the presence of the superheated steam, the flesh, muscles, ligaments, organs and other soft tissue of the body of the deceased (collectively referred to as "pela") soften and separate or detach from the bone structure. The pela falls from the body in pieces. Smaller pieces of pela fall through the wire mesh of tray 20, through funnel 40 and are collected in container 42. Larger pieces of pela may be temporarily caught by the wire mesh, but eventually disintegrate in the presence of the superheated steam and ultimately fall through to container 42. Container 42 is sized to collect the pela from a body of 400 lbs; the maximum capacity for chamber 12.

The steaming process should continue until the pela is completely removed from the body of the deceased, leaving the bones clean, with no remaining tissue or residue. The process may take 4-5 hours until all the pela is detached and removed from the body and collected in container 42. Other temperatures of steam and mass flow rates can be used in the steamatory. The length of time needed for the steaming process to detach the pela from the body depends in part on the steam temperature and mass flow rate. Container 42 is removed from the steamatory and the pela is incinerated or disposed of in a clean, safe, and non-polluting manner.

Only the bone structure of the deceased remains on tray 20. The bone structure remains intact and undisturbed from the placement of the body. The pela has been removed with minimal handling of the body. Moreover, the superheated steaming process maintains the moisture in the bone. Because the iwi (bone) contains the mana (spiritual energy; essence) of the person, the feature of maintaining a moist environment is important as it is desirable that the bone not dry out during the process. The moisture content of the steam ensures that the mana remains within the bone during the process of removing the pela from the bone.

After the pela has been removed from the bone, door 14 is opened and tray 20 slides out to permit removal of the bone structure of the deceased for burial. The family makes final arrangements for burial of the bones.

Following removal of the body from chamber 12, the steaming process can be repeated without a body in the steamatory as a self-cleaning process in preparation for the next usage.

Figure 2:
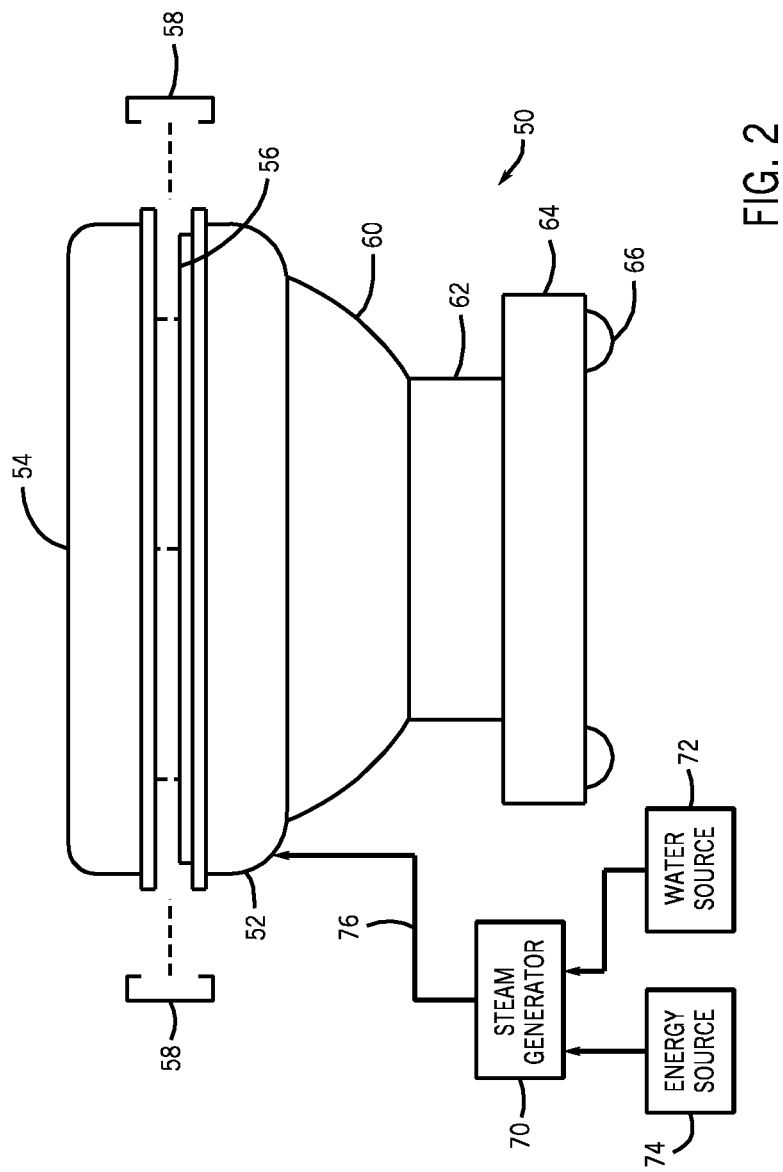
FIG. 2 illustrates an alternate embodiment of the steamatory.

Another embodiment of the steamatory is shown in FIG. 2. Vessel 50 is oval or egg-shaped and includes a lower portion or pan 52 and an upper portion or lid 54. Vessel 50 is made with a similar material and size requirements as described in FIG. 1. A wire-mesh tray 56 is placed inside vessel 50. Lid 54 is placed on pan 52 and sealed with clamps 58. A funnel or contoured structure 60 is integrated into pan 42 and opens into collection container 62. The steamatory is supported by cart 64 having wheels 66.

The body of the deceased is disrobed and wrapped with kapa, tissue, paper, or other degradable material, which breaks down and disintegrates in the presence of heat and steam. Lid 54 is removed to accept the body into vessel 50. The body is carefully laid on tray 56. Alternatively, the disrobed body is laid on kapa cloth, made from the specially prepared bark of the paper mulberry tree or degradable material and further covered by the same material. Lid 54 is re-installed on pan 52 and sealed with clamps 58.

A plurality of steam jets line the interior walls of vessel 50 for injecting superheated steam into the inner portion thereof. A steam generator 70 receives water from water source 72 and energy from energy source 74. The energy is utilized by steam generator 70 to heat the water in a boiler under pressure to generate steam. The steam is routed from steam generator 70 through conduit 76 to the steamatory.

With the body of the deceased sealed inside, the steam enters the inner portion of vessel 50 through the steam jets. In the presence of the superheated steam, the kapa and/or degradable material covering the body breaks down and disintegrates. The degrading body-covering material falls through the wire mesh of tray 56 into funnel 60. The degrading material continues through funnel 60 into collection container 62. In addition to the degrading body-covering material, in the presence of the superheated steam, the pela softens, separates and detaches from the bone structure. The pela falls from the body in pieces and is collected in container 62.

After the pela is detached and removed from the body of the deceased, vessel 50 is opened and the bone structure of the deceased is removed from tray 56 for burial. The family makes final arrangements for burial of the bones. Again, the pela has been removed with minimal handling of the body. Moreover, the superheated steaming process maintains the moisture in the bone. The mana is preserved in the bone structure in accordance with cultural belief. Container 62 is removed from the steamatory and the pela is incinerated or disposed of in a clean, safe, and non-polluting manner. The steamatory is cleaned in preparation for the next usage.

A person skilled in this practice will recognize that changes can be made in form and detail, and equivalents may be substituted for elements of the invention without departing from the scope and spirit of the invention. The present description is therefore considered in all respects to be illustrative and not restrictive, the scope of the invention being determined by the following claims and their equivalents as supported by the above disclosure and drawings.

What is claimed is:

1. A method comprising:
placing a human body, weighing up to 400 pounds and having an amount of tissue on a plurality of bones, on at least one of a plurality of wire mesh layers, wherein:
the plurality of wire mesh layers:
are disposed on a plurality of rollers that are coupled to an interior surface of a chamber;
are configured to slide, on the plurality of rollers, into and out of the chamber; and
include graduating sizes of mesh openings from 0.5 inches to 0.125 inches and at least 2.0 inches of clearance between each of the plurality of wire mesh layers;
a steam generator is coupled, and provides steam, to a plurality of steam jets lining the interior surface of the chamber; and
a container is disposed beneath the plurality of wire mesh layers and sized to collect the amount of tissue;
sliding at least one of the plurality of wire mesh layers' into the chamber; and
dispensing steam into the chamber with a mass flow rate of at least 1000 pounds per hour while collecting the amount of tissue in the container until the plurality of bones are substantially free of the amount of tissue.

2. One or more bones prepared by the method of claim 1.

3. A method comprising:
placing a body, having an amount of tissue supported by a plurality of bones, on a tray;
sliding the tray into a chamber sized to accommodate a human body weighing up to 400 pounds; and
dispensing steam into the chamber through a plurality of steam jets lining an interior surface of the chamber to separate the amount of tissue from the plurality of bones, wherein the plurality of steam jets dispense steam with a mass flow rate of at least 1000 pounds per hour.

4. The method of claim 3, including subjecting the body to the steam until the plurality of bones are substantially free of the amount of tissue.

5. The method of claim 3, wherein:
the tray includes a plurality of wire mesh layers disposed on a plurality of rollers;
the plurality of rollers are coupled to the interior surface of the chamber;
the plurality of wire mesh layers:
are configured to slide independently into and out of the chamber; and
have graduating sizes of mesh openings from about 0.5 inches to about 0.125 inches and at least 2.0 inches of clearance between each of the plurality of wire mesh layers.

6. The method according to claim 3, including collecting the amount of tissue in a container, wherein the container is sized to contain a quantity of tissue from a human body weighing up to 400 pounds.

7. The method according to claim 3, including routing a flow of steam to the plurality of steam jets.

8. The method of claim 3, wherein an amount of steam dispensed into the chamber is selected to maintain a moisture content of the plurality of bones.

9. The method of claim 3, including subjecting the body to the steam until the plurality of bones are substantially free of the amount of tissue, wherein the plurality of steam jets dispense steam with a mass flow rate of at least 1000 pounds per hour.

10. The method of claim 3, including:
routing a flow of steam to the plurality of steam jets; and
subjecting the body to the steam until the plurality of bones are free of the amount of tissue, wherein the plurality of steam jets dispense steam with a mass flow rate of at least 1000 pounds per hour.

11. The method of claim 3, including subjecting the body to the steam until the plurality of bones are substantially free of the amount of tissue, wherein:
the plurality of steam jets dispense steam with a mass flow rate of at least 1000 pounds per hour; and
an amount of steam dispensed into the chamber is selected to maintain a moisture content of the plurality of bones.

12. The method of claim 3, including:
routing steam to the plurality of steam jets; and subjecting the body to the steam until the bones are free of the amount of tissue, wherein:
the plurality of steam jets dispense steam at about 212 degrees Fahrenheit and with a mass flow rate of at least 1000 pounds per hour; and
an amount of steam dispensed into the chamber is selected to maintain a moisture content of the plurality of bones.

13. The method of claim 3, including collecting the amount of tissue in a container, wherein:
the container is sized to contain the amount of tissue from a human body weighing up to 400 pounds;
the tray includes a plurality of wire mesh layers disposed on a plurality of rollers;
the plurality of rollers being coupled to the interior surface of the chamber;
the plurality of wire mesh layers being configured to slide independently into and out of the chamber; and
the plurality of wire mesh layers having graduating sizes of mesh openings from about 0.5 inches to about 0.125 inches and at least 2.0 inches of clearance between each of the plurality of wire mesh layers.

14. The method of claim 3, including:
subjecting the body to the steam until the bones are free of the amount of tissue; and
collecting the amount of tissue in a container, wherein:
the plurality of steam jets dispense steam with a mass flow rate of at least 1000 pounds per hour;
the container is sized to contain the amount of tissue from a human body weighing up to 400 pounds;
the tray includes a plurality of wire mesh layers disposed on a plurality of rollers;
the plurality of rollers being coupled to the interior surface of the chamber;
the plurality of wire mesh layers being configured to slide independently into and out of the chamber; and
the plurality of wire mesh layers having graduating sizes of mesh openings from about 0.5 inches to about 0.125 inches and at least 2.0 inches of clearance between each of the plurality of wire mesh layers.

15. The method of claim 3, including:
routing a flow of steam to the plurality of steam jets;
subjecting the body to the steam until the bones are free of the amount of tissue; and
collecting the amount of tissue in a container, wherein:

the plurality of steam jets dispense steam at about 212 degrees Fahrenheit and with a mass flow rate of at least 1000 pounds per hour;

the container is sized to contain the amount of tissue from a human body weighing up to 400 pounds;

the tray includes a plurality of wire mesh layers disposed on a plurality of rollers;

the plurality of rollers being coupled to the interior surface of the chamber;

the plurality of wire mesh layers being configured to slide independently into and out of the chamber; and the plurality of wire mesh layers having graduating sizes of mesh openings from about 0.5 inches to about 0.125 inches and at least 2.0 inches of clearance between each of the plurality of wire mesh layers.

16. The method of claim 3, including:

routing a flow of steam to the plurality of steam jets;

subjecting the body to the steam until the bones are free of the amount of tissue; and collecting the amount of tissue in a container, wherein:

the plurality of steam jets dispense steam with a mass flow rate of at least 1000 pounds per hour;

an amount of steam dispensed into the chamber is selected to maintain a moisture content of the plurality of bones;

the container is sized to contain the amount of tissue from a human body weighing up to 400 pounds;

the tray includes a plurality of wire mesh layers disposed on a plurality of rollers;

the plurality of rollers being coupled to the interior surface of the chamber;

the plurality of wire mesh layers being configured to slide independently into and out of the chamber; and the plurality of wire mesh layers having graduating sizes of mesh openings from about 0.5 inches to about 0.125 inches and at least 2.0 inches of clearance between each of the plurality of wire mesh layers.

17. A method comprising:

providing a cylindrical vessel, wherein the cylindrical vessel includes a chamber sized to accommodate a human body weighing up to 400 lbs;

mounting a plurality of rollers to an interior surface of the chamber;

disposing a plurality of wire mesh layers on the plurality of rollers in the chamber, the plurality of wire mesh layers having graduating sizes of mesh openings from 0.5 inches to 0.125 inches and at least 2.0 inches of clearance between each of the plurality of wire mesh layers;

coupling a plurality of steam jets to the interior surface of the chamber, the plurality of steam jets being configured to dispense steam into the chamber with a mass flow rate of at least 1000 pounds per hour;

connecting a steam generator to the plurality of steam jets, wherein the steam generator is configured to provide steam for a time period between four and five hours;

coupling a funnel to the chamber beneath at least one of the plurality of wire mesh layers, wherein the funnel is configured to channel an amount of tissue of a body after falling through the plurality of wire mesh layers; and disposing a container beneath the funnel for collecting the amount of tissue, wherein the container is sized to collect a quantity of tissue from a human body weighing up to 400 pounds.

18. A steamatory formed by the method of claim 17.

* * * * *